(12) United States Patent
Solem et al.

(10) Patent No.: US 7,637,945 B2
(45) Date of Patent: *Dec. 29, 2009

(54) DEVICE AND METHOD FOR TREATMENT OF MITRAL INSUFFICIENCY

(75) Inventors: Jan Otto Solem, Stetten (CH); Per Ola Kimblad, Lund (SE)

(73) Assignee: Edwards Lifesciences Corporation, Irvine, CA (US)

( * ) Notice: Subject to any disclaimer, the term of this patent is extended or adjusted under 35 U.S.C. 154(b) by 99 days.

This patent is subject to a terminal disclaimer.

(21) Appl. No.: 11/643,352

(22) Filed: Dec. 20, 2006

(65) Prior Publication Data

US 2007/0100442 A1    May 3, 2007

Related U.S. Application Data

(63) Continuation of application No. 10/953,047, filed on Sep. 29, 2004, now Pat. No. 7,311,728, which is a continuation of application No. 10/019,563, filed as application No. PCT/SE00/01369 on Jun. 28, 2000, now Pat. No. 7,044,967.

(51) Int. Cl.
 *A61F 2/24* (2006.01)
(52) U.S. Cl. ..................... 623/2.36; 623/2.37
(58) Field of Classification Search ........ 623/2.36–2.37
 See application file for complete search history.

(56) References Cited

U.S. PATENT DOCUMENTS

| 4,655,771 A | 4/1987 | Wallsten |
|---|---|---|
| 5,064,435 A | 11/1991 | Porter |
| 5,071,407 A | 12/1991 | Termin et al. |
| 5,170,802 A | 12/1992 | Mehra |
| 5,209,730 A | 5/1993 | Sullivan |
| 5,224,491 A | 7/1993 | Mehra |
| 5,304,131 A | 4/1994 | Paskar |
| 5,382,259 A | 1/1995 | Phelps et al. |
| 5,383,892 A | 1/1995 | Cardon et al. |
| 5,390,661 A | 2/1995 | Griffith et al. |
| 5,441,515 A | 8/1995 | Khosravi et al. |
| 5,449,373 A | 9/1995 | Pinchasik et al. |
| 5,496,275 A | 3/1996 | Sirhan et al. |

(Continued)

FOREIGN PATENT DOCUMENTS

DE        19604042        1/2009

(Continued)

OTHER PUBLICATIONS

Buchanan, et al., Circumferential Suture of the Mitral Annulus for Correction of Mitral Regurgitation in Dogs, Veterinary Surgery, 27:182-193, 1998.

*Primary Examiner*—Suzette J Gherbi
(74) *Attorney, Agent, or Firm*—David L. Hauser; Michael Crapenhoft

(57) ABSTRACT

A device for treatment of mitral annulus dilatation comprises an elongate body having two states. In a first of these states the elongate body is insertable into the coronary sinus and has a shape adapting to the shape of the coronary sinus. When positioned in the coronary sinus, the elongate body is transferable to the second state assuming a reduced radius of curvature, whereby the radius of curvature of the coronary sinus and the radius of curvature as well as the circumference of the mitral annulus is reduced.

9 Claims, 5 Drawing Sheets

U.S. PATENT DOCUMENTS

| | | | |
|---|---|---|---|
| 5,531,779 A | 7/1996 | Dahl et al. |
| 5,545,209 A | 8/1996 | Roberts et al. |
| 5,591,197 A | 1/1997 | Orth et al. |
| 5,607,444 A | 3/1997 | Lam |
| 5,713,949 A | 2/1998 | Jayaraman |
| 5,817,126 A | 10/1998 | Imran |
| 5,876,433 A | 3/1999 | Lunn |
| 5,891,108 A | 4/1999 | Leone et al. |
| 5,935,081 A | 8/1999 | Kadhiresan |
| 5,954,761 A | 9/1999 | Machek et al. |
| 5,961,545 A | 10/1999 | Lentz et al. |
| 5,980,522 A | 11/1999 | Koros et al. |
| 6,006,122 A | 12/1999 | Smits |
| 6,013,854 A | 1/2000 | Moriuchi |
| 6,019,739 A | 2/2000 | Rhee et al. |
| 6,051,020 A | 4/2000 | Golcoechea et al. |
| 6,077,296 A | 6/2000 | Shokoohi et al. |
| 6,093,203 A | 7/2000 | Uflacker |
| 6,110,100 A | 8/2000 | Talpade |
| 6,123,699 A | 9/2000 | Webster, Jr. |
| 6,161,029 A | 12/2000 | Spreigl et al. |
| 6,161,543 A | 12/2000 | Cox et al. |
| 6,165,169 A | 12/2000 | Panescu et al. |
| 6,168,619 B1 | 1/2001 | Dinh et al. |
| 6,171,329 B1 | 1/2001 | Shaw et al. |
| 6,210,432 B1 | 4/2001 | Solem et al. |
| 6,629,534 B1 | 10/2003 | St. Goar et al. |
| 6,997,951 B2 | 2/2006 | Solem et al. |
| 7,044,967 B1 | 5/2006 | Solem et al. |
| 7,090,695 B2 | 8/2006 | Solem et al. |
| 7,311,728 B2 * | 12/2007 | Solem et al. ............... 623/2.36 |
| 2001/0018611 A1 | 8/2001 | Solem et al. |
| 2002/0111647 A1 | 8/2002 | Khairkhahan et al. |
| 2003/0204138 A1 | 10/2003 | Choi |
| 2004/0073302 A1 | 4/2004 | Rourke et al. |
| 2004/0102840 A1 | 5/2004 | Solem et al. |
| 2005/0043792 A1 | 2/2005 | Solem et al. |
| 2006/0116756 A1 | 6/2006 | Solem et al. |

FOREIGN PATENT DOCUMENTS

| | | |
|---|---|---|
| EP | 0955017 | 4/1999 |
| WO | WO 96/34211 | 10/1996 |
| WO | WO 99/33534 | 9/1999 |
| WO | WO 00/01320 | 4/2000 |
| WO | WO 01/00111 | 1/2001 |
| WO | WO 03/055417 | 7/2003 |

* cited by examiner

DEVICE AND METHOD FOR TREATMENT
OF MITRAL INSUFFICIENCY

REFERENCE TO RELATED APPLICATIONS

The present application is a continuation of U.S. patent application Ser. No. 10/953,047, filed Sep. 29, 2004 now U.S. Pat. No. 7,311,728, which is a continuation of U.S. patent application Ser. No. 10/019,563, filed Jul. 1, 2002, now U.S. Pat. No. 7,044,967, which is a national stage under 35 U.S.C. §371 of international application PCT/SE00/01369, filed Jun. 28, 2000 which designated the United States, and which international application was published under PCT Article 21(2) in the English language and which claims priority to SE 9902455-6, filed Jun. 29, 1999, the disclosures of which are incorporated fully herein by reference.

FIELD OF THE INVENTION

The present invention generally relates to a device and a method for treatment of mitral insufficiency and, more specifically, for treatment of dilatation of the mitral annulus.

BACKGROUND

Mitral insufficiency can result from several causes, such as ischemic disease, degenerative disease of the mitral apparatus, rheumatic fever, endocarditis, congenital heart disease and cardiomyopathy. The four major structural components of the mitral valve are the annulus, the two leaflets, the chordae and the papillary muscles. Any one or all of these in different combinations may be injured and create insufficiency. Annular dilatation is a major component in the pathology of mitral insufficiency regardless of cause. Moreover, many patients have a mitral insufficiency primarily or only due to posterior annular dilatation, since the annulus of the anterior leaflet does not dilatate because it is anchored to the fibrous skeleton of the base of the heart.

Studies of the natural history of mitral insufficiency have found that totally asymptomatic patients with severe mitral insufficiency usually progress to severe disability within five years. At present the treatment consists of either mitral valve replacements or repair, both methods requiring open heart surgery. Replacement can be performed with either mechanical or biological valves.

The mechanical valve carries the risk of thromboembolism and requires anticoagulation, with all its potential hazards, whereas biological prostheses suffer from limited durability. Another hazard with replacement is the risk of endocarditis. These risks and other valve related complications are greatly diminished with valve repair.

Mitral valve repair is theoretically possible if an essentially normal anterior leaflet is present. The basic four techniques of repair include the use of an annuloplasty ring, quadrangular segmental resection of diseased posterior leaflet, shortening of elongated chordae, and transposition of posterior leaflet chordae to the anterior leaflet.

Annuloplasty rings are needed to achieve a durable reduction of the annular dilatation. All the common rings are sutured along the posterior mitral leaflet adjacent to the mitral annulus in the left atrium. The Duran ring encircles the valve completely, whereas the others are open towards the anterior leaflet. The ring can either be rigid, like the original Carpentier ring, or flexible but non-elastic, like the Duran ring or the Cosgrove-Edwards ring.

Effective treatment of mitral insufficiency currently requires open-heart surgery, by the use of total cardiopulmonary by-pass, aortic cross-clamping and cardioplegic arrest.

To certain groups of patient, this is particular hazardous. Elderly patients, patients with a poor left ventricular function, renal disease, severe calcification of the aorta, previous cardiac surgery or other concomitant diseases, would in particular most likely benefit from a less invasive approach, even if repair is not complete. The current trend towards less invasive coronary artery surgery, without cardiopulmonary by-pass, as well as PTCA will also call for a development of a less invasive method for repair of the often concomitant mitral insufficiency.

SUMMARY

A first object of the present invention is to provide a device and a method for treatment of mitral insufficiency without the need for cardiopulmonary by-pass and opening of the chest and heart.

A second object of the invention is to provide reduction of the mitral annulus using less invasive surgery.

According to the present invention, a device for treatment of mitralis insufficiency comprises an elongate body having such dimensions as to be insertable into the coronary sinus and having two states, in a first state of which the elongate body has a shape that is adaptable to the shape of the coronary sinus, and to the second state of which the elongate body is transferable from the said first state assuming a reduced radius of curvature, whereby the radius of curvature of the coronary sinus is reduced as well as the circumference of the mitral valve annulus, when the elongate body is positioned in the coronary sinus.

Preferably, means are provided for the transfer of the elongate body to the second state by bending and/or shortening it from a larger radius of curvature to a smaller radius of curvature.

The transfer means may comprise-means for bending and/or shortening the elongate body by a preferably asymmetric contraction thereof.

Further, the elongate body may comprise a memory material providing the transfer to the second state.

In a preferred embodiment, the elongate body may comprise a stent. In an alternative embodiment, the device according to the invention may comprise several stent sections and said bending and/or shortening means may comprise wires for shortening the distance between the stent sections.

According to a second aspect, a method of reducing the circumference of the mitral valve annulus comprises the steps of inserting an elongate body into the coronary sinus in the vicinity of the posterior leaflet of the mitral valve, and then providing a bending and/or shortening of the elongate body when positioned in the coronary sinus so as to reduce the curvature of the coronary sinus and thereby reduce the circumference of the mitral valve annulus.

Thus, the present invention takes advantage of the position of the coronary sinus being close to the mitral annulus. This makes repair possible by the use of current catheter-guided techniques.

The coronary veins drain blood from the myocardium to the right atrium. The smaller veins drain blood directly into the atrial cavity, and the larger veins accompany the major arteries and run into the coronary sinus which substantially encircles the mitral orifice and annulus. It runs in the posterior atrioventricular groove, lying in the fatty tissue between the left atrial wall and the ventricular myocardium, before draining into the right atrium between the atrial septum and the post-Eustachian sinus.

In an adult, the course of the coronary sinus may approach within 5-15 mm of the medial attachment of the posterior leaflet of the mitral valve. Preliminary measurements performed at autopsies of adults of normal weight show similar results, with a distance of 5.3±0.6 mm at the medial attachment and about 10 mm at the lateral aspect of the posterior leaflet. The circumference of the coronary sinus was 18.3±2.9 mm at its ostium (giving a diameter of the posterior leaflet of 5.8±0.9 mm) and 9.7±0.6 mm along the lateral aspect of the posterior leaflet (corresponding to a diameter of 3.1±0.2 mm).

BRIEF DESCRIPTION OF THE DRAWINGS

The invention will be better understood by the following description of preferred embodiments referring to the appended drawings, in which.

DETAILED DESCRIPTION

Figure 1:
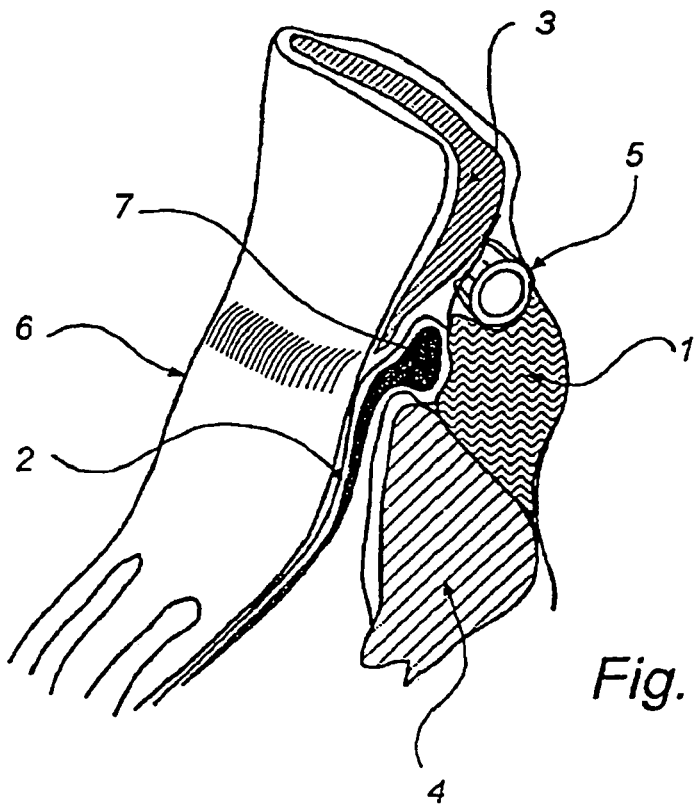
FIG. 1 is a cross-sectional view of a part of a heart.

FIG. 1 is a cross-sectional view through the heart area of the posterior atrioventricular groove 1, which is filled with fatty tissue. It shows the posterior leaflet 2 of the mitral valve and the adjoining parts 3, 4 of the atrial myocardium and the ventricular myocardium. The coronary sinus 5 is shown close to the mitral annulus 6 and behind the attachment 7 of the posterior leaflet 2. Since the coronary sinus 5 substantially encircles the mitral annulus 6, a reduction of the radius of curvature of the bent coronary sinus 5 also will result in a diameter-and circumference reduction of the mitral annulus 6.

Figure 2:
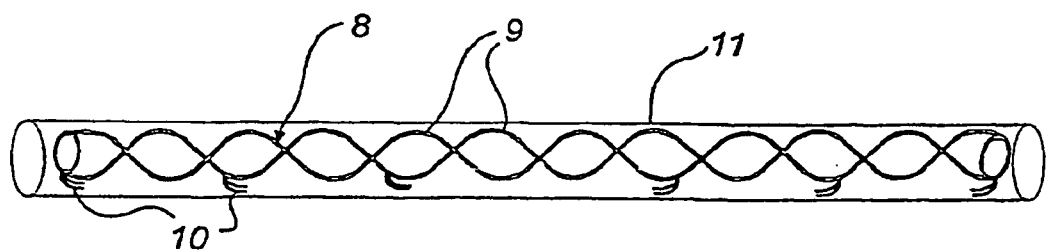
FIGS. 2 and 3 are schematic views of a first embodiment of a device according to the present invention.
Figure 3:
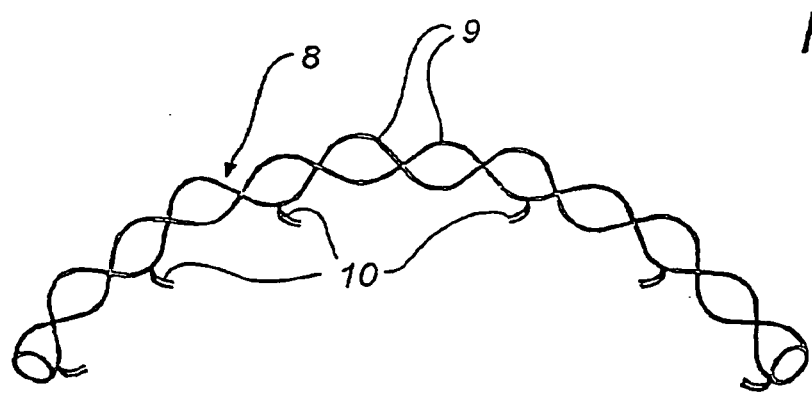

The device of FIG. 2 comprises an elongate body 8 made of memory metal, e.g. Nitinol, or other similar material which has a memory of an original shape, illustrated in FIG. 3, and can be temporary forced into another shape, illustrated in FIG. 2. This elongate body 8 comprises one, two or more memory metal strings 9 of helical or other shape so as to fit together and be able of permitting the movements described below. Along the elongate body 8 several hooks 10 are fastened so as to extend radially out therefrom. These hooks 10 are covered by a cover sheet 11 in FIG. 2.

Figure 4:
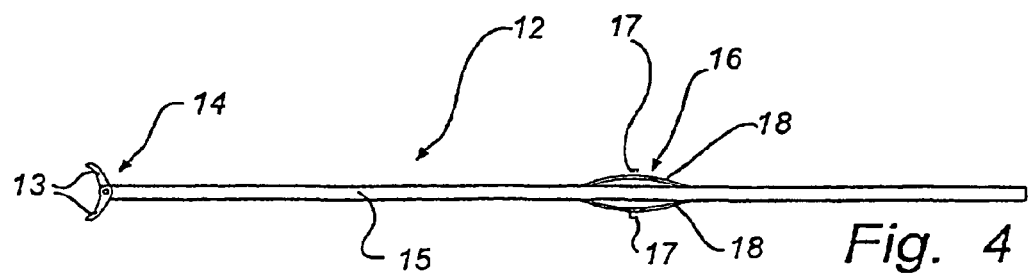
FIGS. 4-6 are schematic views illustrating an instrument, which may be used when positioning the device shown in FIGS. 2 and 3 in the coronary sinus.

The elongate body 8 is forced into a stretched or extended state by means of a stabilizing instrument 12 shown in FIG. 4. This instrument 12 has two arms 13 at a distal end 14 of a rod 15 and a locking means 16 at a proximal end of the rod 15. The distance between the ends of the rod 15 corresponds to the desired length of the elongate body 8 when being inserted into the coronary sinus 5.

Figure 5:
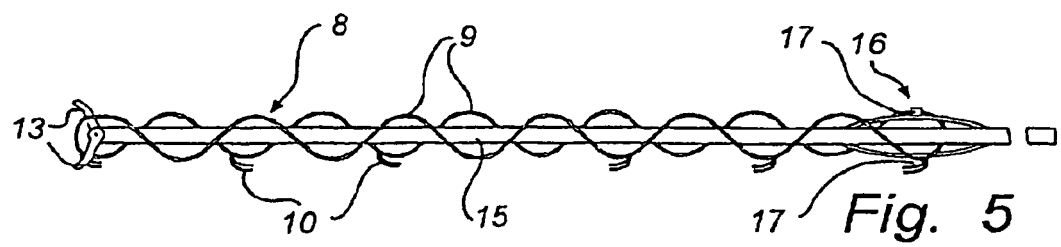
Figure 6:
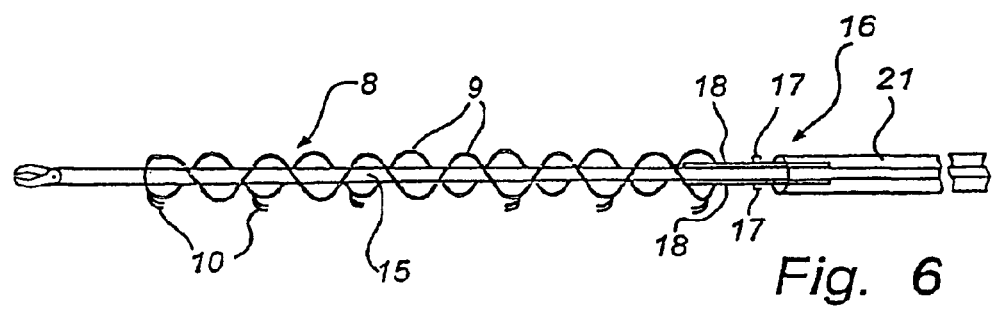

The arms 13 are free to move between the position shown in FIG. 4 and a position in alignment with the rod 15, as shown in FIG. 6. The locking means 16 has two locking knobs 17, which are pressed radially outwards from the rod 15 by two spring blades 18. Thus, the elongated body 8 can be pushed over the rod 15 of the stabilizing instrument 12, then stretched between the arms 13 and the knobs 17, and finally locked in its stretched state on the stabilizing instrument 12 between the arms 13 and the knobs 17, as illustrated in FIG. 5.

The rod 15 may be a metal wire which is relatively stiff between the distal end 14 and the locking means 16 but still so bendable that it will follow the shape of the coronary sinus 5. Proximally of the locking means 16 the metal wire of the stabilizing instrument 11 is more pliable to be able to easily follow the bends of the veins.

The above-described elongate body 8 is positioned in the coronary sinus 5 in the following way:

An introduction sheet (not shown) of synthetic material may be used to get access to the venous system. Having reached access to the venous system, a long guiding wire (not shown) of metal is advanced through the introduction sheet and via the venous system to the coronary sinus 5. This guiding wire is provided with X-ray distance markers so that the position of the guiding wire in the coronary sinus 5 may be monitored.

Figure 8:
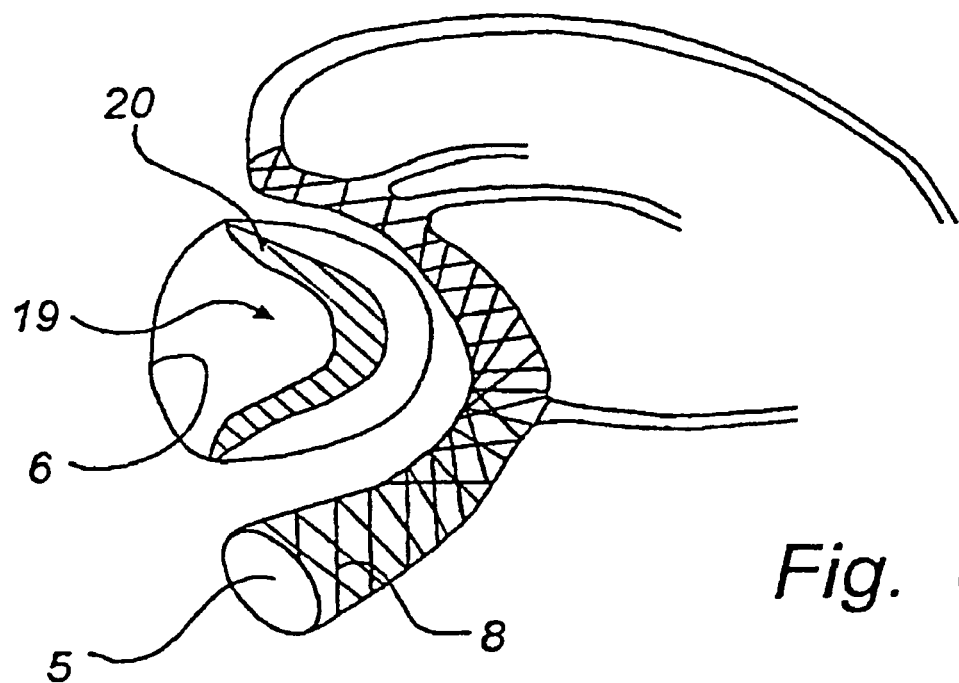
FIGS. 8 and 9 are schematic views illustrating the positioning of the device of FIGS. 2 and 3 in the coronary sinus.

The elongate body 8 is locked onto the stabilizing instrument 12, as shown in FIG. 5, and introduced into the long cover sheet 11 of synthetic material. This aggregate is then pushed through the introduction sheet and the venous system to the coronary sinus 5 riding on the guiding wire. After exact positioning of the elongate body 8 in the coronary sinus 5, as illustrated in FIG. 8 where the mitral valve 19 is shown having a central gap 20, the cover sheet 11 is retracted exposing the elongate body 8 within the coronary sinus 5. This manoeuvre allows the hooks 10 on the elongate body 8 to dig into the walls of the coronary sinus 5 and into the heart. The elongate body 8 is still locked on to the stabilizing instrument 12 such that the hooks 10 engage the walls of the coronary sinus 5 in the stretched or extended state of the elongate body 8.

Figure 9:
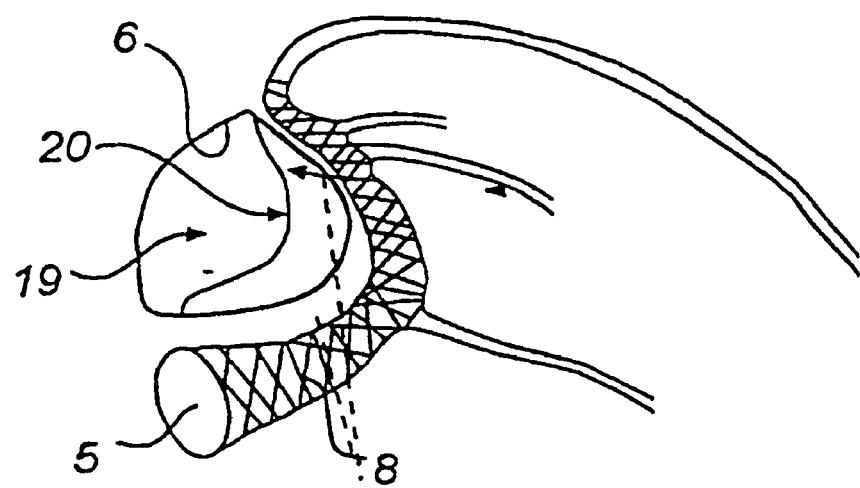

A catheter 21, shown in FIG. 6, is pushed forward on the guiding wire and the rod 15 for releasing the elongate body 8 from the locking means 16 by pressing the spring blades 18 towards the rod 15. This movement releases the knobs 17 as well as the arms 13 from engagement with the elongate body 8 which contracts as illustrated in FIG. 9 and as a result bends towards the mitral valve annulus 6 moving the posterior part thereof forward (shown by arrows in FIG. 9). This movement reduces the circumference of the mitral valve annulus 6 and thereby closes the central gap 20.

Figure 7:
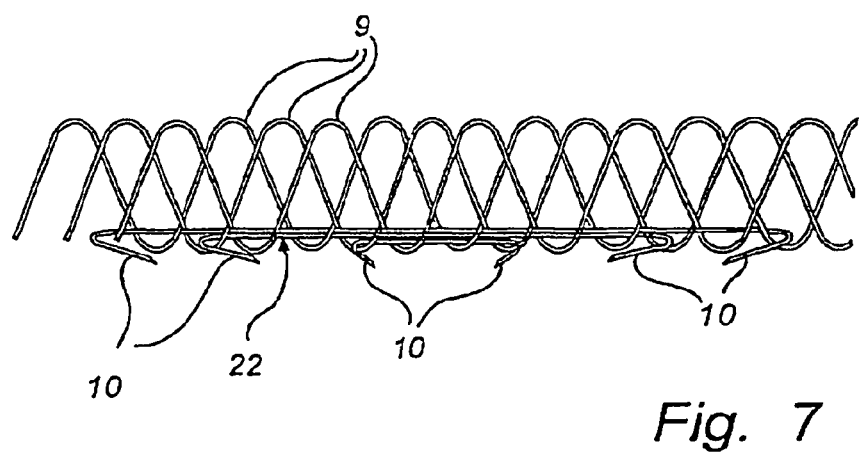
FIG. 7 is a partial, enlarged view of the first embodiment shown in FIG. 2.

FIG. 7 illustrates a part of an arrangement of the wires 9 and the hooks 10 along a peripheral part of the elongate body 8, whereby the elongate body 8 will be asymmetrically contracted resulting in a bending thereof when interconnecting parts 22 of at least some of the hooks 10 are shortened to an original shape.

Figure 10:
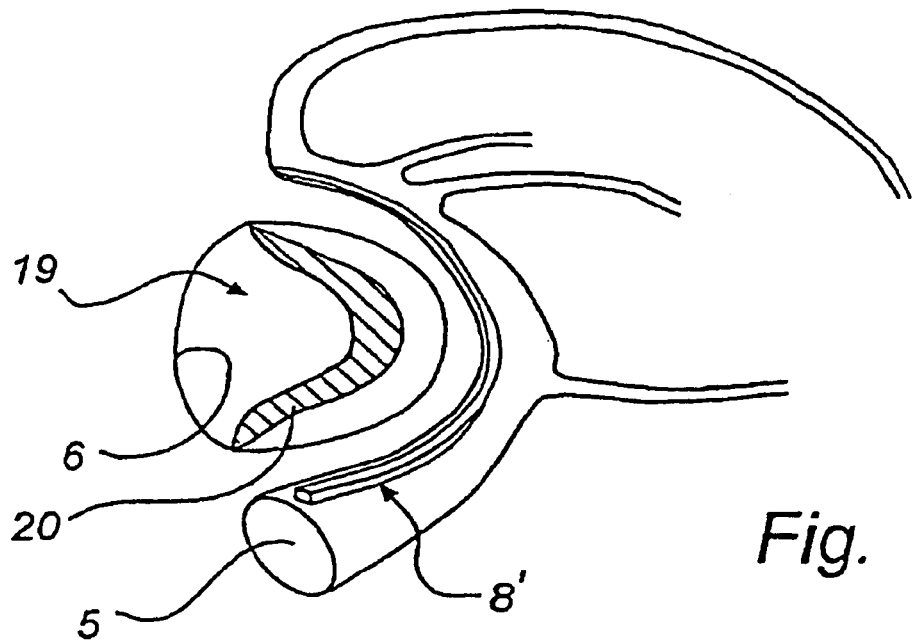
FIGS. 10 and 11 are schematic views illustrating the positioning of a second embodiment of the device according to the present invention in the coronary sinus.
Figure 11:
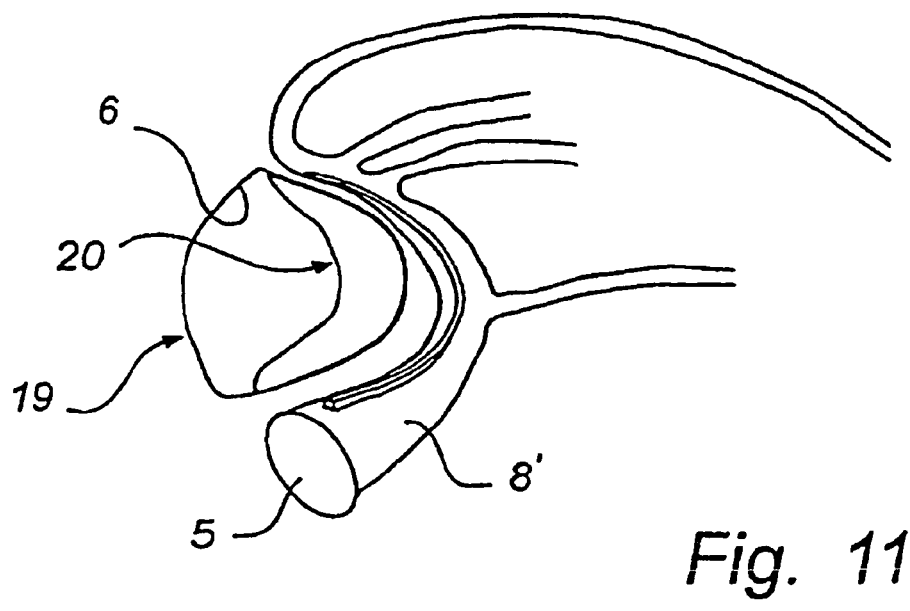

FIGS. 10 and 11 illustrate an alternative embodiment of an elongate body 8', which is a solid wire in the shape of an open U-shaped ring that will engage the wall of the coronary sinus 5 most adjacent to the mitral valve annulus 6 when inserted into the coronary-sinus 5. The elongate body 8' consists of a memory metal material which when reverting to its original shape will bend as illustrated in FIG. 11. The return of the open ring 8' to its original shape may be initiated in several ways, as is obvious to the man skilled in the art.

Figure 12:
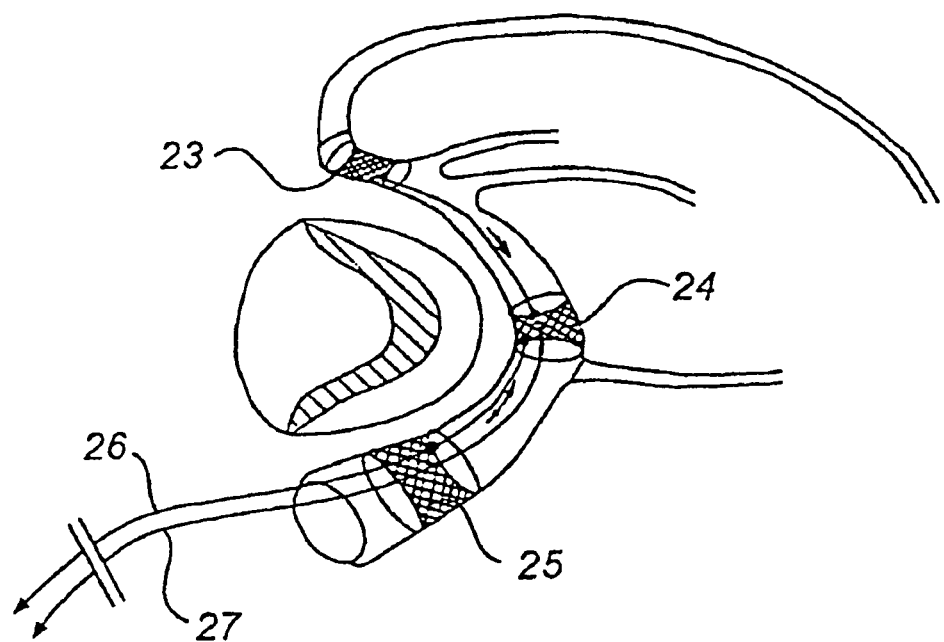
FIGS. 12 and 13 are schematic views illustrating the positioning of a third embodiment of the device according to the present invention in the coronary sinus.
Figure 13:
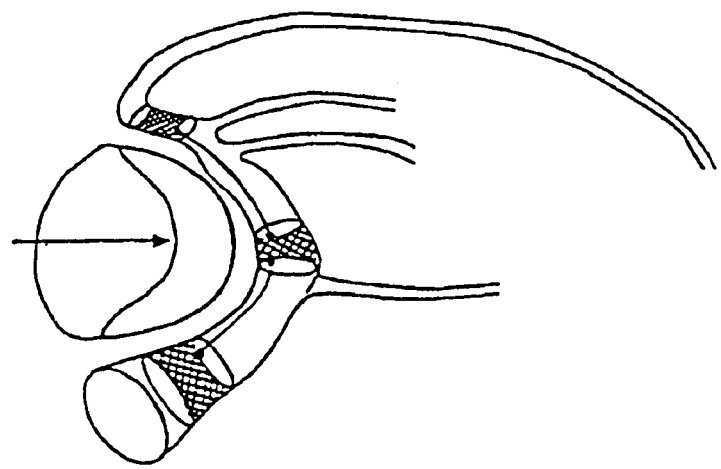

The third embodiment of the elongate body 8", illustrated in FIGS. 12 and 13, comprises three stent sections 23 25 positioned at one end of the elongate body 8", at the middle thereof and at the other end of the elongate body 8", respectively. These stent sections 23 25 may be positioned in the coronary sinus 5 as illustrated by conventional means, such that their positions are fixed. They are connected by wires 26, 27, which may be maneuvered from outside the vein system such that the distances between the adjacent stent sections 23, 24 and 24, 25 are reduced. More specifically, these distances are reduced asymmetrically, i.e. more on the side of coronary sinus 5 most adjacent to the posterior part of the mitral valve annulus 6. Thereby, the elongate body 8" is bent, as illustrated in FIG. 13, and presses the coronary sinus 5 against the mitral valve annulus 6 closing the gap 20.

Concludingly, the present invention provides a device placed in the coronary sinus, designed to reduce the dilatation of the mitral annulus. This device is at a distance from the attachment of the posterior leaflet that does not much exceed the distance at which present annuloplasty rings are placed by open surgery techniques, and the coronary sinus is along its entire course large enough to hold such a device. The device could be positioned by catheter technique or any other adequate technique and offers a safer alternative to the current open surgery methods. The device could be designed or heparincoated so as to avoid thrombosis in the coronary sinus, thus reducing the need for aspirin, ticlopedine or anticoagulant therapy.

It is to be understood that modifications of the above-described device and method can be made by people skilled in the art without departing from the spirit and scope of the invention.

What is claimed is:

1. A system for treatment of mitral valve dilatation, comprising:
    an elongate body including a distal anchor configured to be positioned within and anchored to a coronary sinus of a heart adjacent to a mitral valve annulus within the heart, a proximal anchor configured to be positioned within the heart proximal to the distal anchor and adjacent to the mitral valve annulus within the heart, and an interconnecting part permanently attached to the distal and proximal anchors;
    a cover sheet having a distal end, a proximal end and a lumen that receives the elongate body, the cover sheet being guidable into the coronary sinus adjacent to the mitral valve annulus and being retractable for deploying the distal and proximal anchors of the device within the coronary sinus adjacent to the mitral valve annulus; and
    a detachable delivery instrument coupled to at least the proximal anchor of the elongate body and extending proximally though the lumen and out of the catheter proximal end, the delivery instrument being configured for positioning and releasing the elongate body in the coronary sinus;
    wherein the elongate body is configured to effect the shape of the mitral valve annulus after deployment in the coronary sinus.

2. The system of claim 1 whereby, when the distal anchor is released from the cover sheet in the coronary sinus, the proximal anchor may be displaced proximally by proximally pulling on the delivery instrument to effect the shape of the mitral valve annulus and thereafter released to maintain the effect on the mitral valve annulus.

3. The system of claim 1 wherein the proximal anchor, when deployed, is anchored against distal movement and moveable in a proximal direction.

4. The system of claim 1 wherein the distal anchor is self deploying upon release in the coronary sinus.

5. The system of claim 1 wherein the proximal anchor is self-deploying upon release in the coronary sinus.

6. The system of claim 1 wherein the interconnecting part has a fixed length.

7. The system of claim 6 wherein the interconnecting part is configured to bend to an original shape after implantation, thereby shortening the distance between the distal and proximal anchors.

8. The system of claim 1 wherein the interconnecting member is stretchable to a maximum length.

9. The system of claim 1 wherein the interconnecting member is bendable and non-stretchable.

* * * * *

UNITED STATES PATENT AND TRADEMARK OFFICE
CERTIFICATE OF CORRECTION

PATENT NO.      : 7,637,945 B2
APPLICATION NO. : 11/643352
DATED           : December 29, 2009
INVENTOR(S)     : Solem et al.

Page 1 of 1

It is certified that error appears in the above-identified patent and that said Letters Patent is hereby corrected as shown below:

Title Page

Item (73) The assignee should read as follows:

Edwards Lifesciences ~~Corporation~~ AG

Title Page

Please correct Item (63) the related U.S. Application Data:

Continuation of Application No. 10/953,047, filed on Sep. 29, 2004, now Pat. No. 7,311,728, which is a continuation of Application No. 10/019,563, <u>filed July 1, 2002, now Pat No. 7,044,967,</u> filed as Application No. PCT/SE00/01369 on Jun. 28, 2000, now Pat. No. 7,044,967.

Title Page

Add Item (30):

--Foreign Application Priority Data

SE 9902455-6, filed June 29, 1999--

Signed and Sealed this
Third Day of July, 2012

David J. Kappos
*Director of the United States Patent and Trademark Office*